United States Patent [19]
Grant

[11] 4,283,276
[45] Aug. 11, 1981

[54] ROTOR FOR SEDIMENTATION FIELD FLOW FRACTIONATION

[75] Inventor: John W. Grant, Chadds Ford, Pa.

[73] Assignee: E. I. Du Pont de Nemours and Company, Wilmington, Del.

[21] Appl. No.: 125,855

[22] Filed: Feb. 29, 1980

[51] Int. Cl.³ .............................................. B03B 5/62
[52] U.S. Cl. ................................ 209/155; 73/432 PS; 233/27
[58] Field of Search ................... 209/1, 155, 208, 444, 209/453, 11; 55/67, 81; 73/432 PS, 23.1; 210/198 C, 72; 233/1 R, 1 A, 1 D, 14 R, 23 R, 25, 26, 27

[56] References Cited
FOREIGN PATENT DOCUMENTS
2002266  2/1979  United Kingdom ...................... 233/27

Primary Examiner—Ralph J. Hill

[57] ABSTRACT

A long, thin annular belt-like channel is designed for use in sedimentation field flow fractionation. This channel, which is the rotor of a centrifuge, is designed to maintain its thickness dimension constant and yet facilitate its manufacture and cleaning by forming the rotor of a double mating ring in which the inner ring is split. This permits the inner ring to conform to the outer load carrying ring.

11 Claims, 5 Drawing Figures

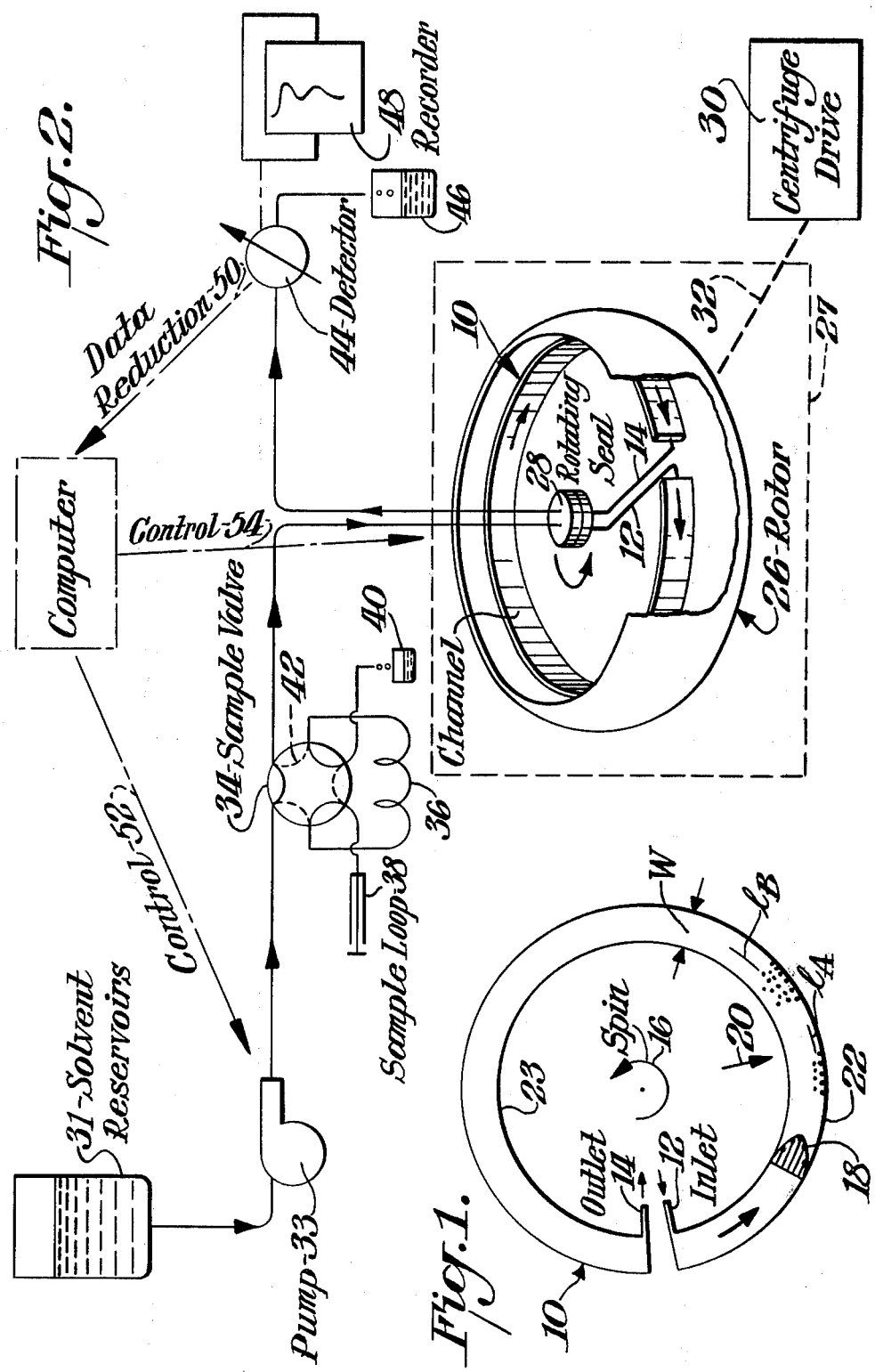

ROTOR FOR SEDIMENTATION FIELD FLOW FRACTIONATION

BACKGROUND OF THE INVENTION

Sedimentation field flow fractionation is a versatile technique for the high resolution separation of a wide variety of particulates suspended in a fluid medium. The particulates including macromolecules in the $10^5$ to the $10^{13}$ molecular weight (0.001 to 1 $\mu$m) range, colloids, particles, micelles, organelles and the like. The technique is more explicitly described in U.S. Pat. No. 3,449,938, issued June 17, 1969 to John C. Giddings and U.S. Pat. No. 3,523,610, issued Aug. 11, 1970 to Edward M. Purcell and Howard C. Berg.

Field flow fractionation is the result of the differential migration rate of components in a carrier or mobile phase in a manner similar to that experienced in chromatography. However, in field flow fractionation there is no separate stationary phase as is in the case of chromatography. Sample retention is caused by the redistribution of sample components between the fast to the slow moving strata within the mobile phase. Thus, particulates elute more slowly than the solvent front. Typically a field flow fractionation channel, consisting of two closely spaced parallel surfaces, is used wherein a mobile phase is caused to flow continuously through the gap between the surfaces. Because of the narrowness of this gap or channel (typically 0.025 centimeters (cm)) the mobile phase flow is laminar with a characteristic parabolic velocity profile. The flow velocity is the highest at the middle of the channel and essentially zero near the two channel surfaces. An external force field of some type (the force fields include gravitational, thermal, electrical, fluid cross flow and others described variously by Giddings and Berg and Purcell), is applied transversely (perpendicular) to the channel surfaces or walls. This force field pushes the sample components in the direction of the slower moving strata near the outer wall. The buildup of sample concentration near the wall, however, is resisted by the normal diffusion of the particulates in a direction opposite to the force field. This results in a dynamic layer of component particles, each component with an exponential—concentration profile. The extent of retention is determined by the particulates time average position within the concentration profile which is a function of the balance between the applied field strength and the opposing tendency of particles to diffuse.

In the case of a sdeimentation force field, which is used in sedimentation field flow fractionation, use is made of a centrifuge to establish the force field. For this purpose a long, thin annular belt-like channel is made to rotate in a centrifuge. The resultant centrifugal force causes components of higher density than the mobile phase to sediment toward the outer wall of the channel. For equal particle density, because of higher diffusion rate, smaller particulates will accumulate into a thicker layer against the outer wall than will larger particles. On the average, therefore, larger particulates are forced closer to the outer wall.

If now the mobile phase or solvent is fed continuously from one end of the channel, it carries the sample components through the channel for later detection at the outlet of the channel. Because of the shape of the laminar velocity profile within the channel and the placement of particulates in that profile, solvent flow causes smaller particulates to elute first, followed by a continuous elution of components in the order of ascending particulate mass.

In order to reduce the separation times required using this technique, it is necessary to make the channels relatively thin as noted. This creates many problems in that the walls of the channel must have a microscopically smooth finish to prevent the particles from sticking to the walls or being trapped in crevices of the same height as the particle distributed. Unfortunately, in the construction of such a thin belt-like channel for use in a centrifuge the microfinish cannot be easily obtained or maintained. Further, one must have access to the inner walls of the channel on occasion for cleaning. Another problem, in order to maintain a high degree of resolution of the separated components of the sample, the channel must maintain a constant thickness during operation even when subjected to large centrifugal forces. Constant channel thickness is difficult to maintain during centrifugation because the outer channel wall tends to enlarge to a greater extent than the inner channel wall. This is particularly true when the channel is formed between mating inner and outer rings. This is not easily accomplished, particularly if the weight of the channel elements are to be maintained at reasonably small values for use in the centrifuge.

SUMMARY OF THE INVENTION

According to one aspect of this invention, an apparatus is constructed for separating particulates suspended in a fluid medium according to their effective masses. This apparatus includes an annular, cylindrical channel having a cylinder axis, means for rotating the channel about the axis, means for passing the fluid medium circumferentially through the channel and means for introducing the particulates into the medium for passage through the channel. This apparatus is improved according to this invention by constructing the channel of a pair of mating rings including an outer support ring and an inner ring, separated at a point along its circumference, mating with the outer ring to define said annular channel.

In one aspect of the invention the inner ring is formed such that its radially outer wall has a circumferential groove of constant depth, the groove constituting the channel. Resilient circumferential seals are positioned between the two rings along the edges of the groove. An orifice through the inner ring adjacent the split afford fluid access to the channel and preferably the inner ring has a radial flange defining an L-shaped cross section whereby the inner ring flange is axially supported by the outer ring. A wedge may frictionally engage the longitudinal end of the inner ring to maintain the inner ring spread even in the absence of centrifugal force. The outer ring can be a bowl like rotor or alternatively can be supported by spokes, a disclike structure, or the like.

BRIEF DESCRIPTION OF THE DRAWINGS

Further advantages and features of this invention will become apparent upon the following description wherein:

FIG. 1 is a simplified schematic representation of the sedimentation field flow fractionation technique;

FIG. 2 is a partially schematic, partially pictorial representation of a particle separation apparatus constructed in accordance with this invention;

DETAILED DESCRIPTION OF THE PREFERRED EMBODIMENT

Figure 3:
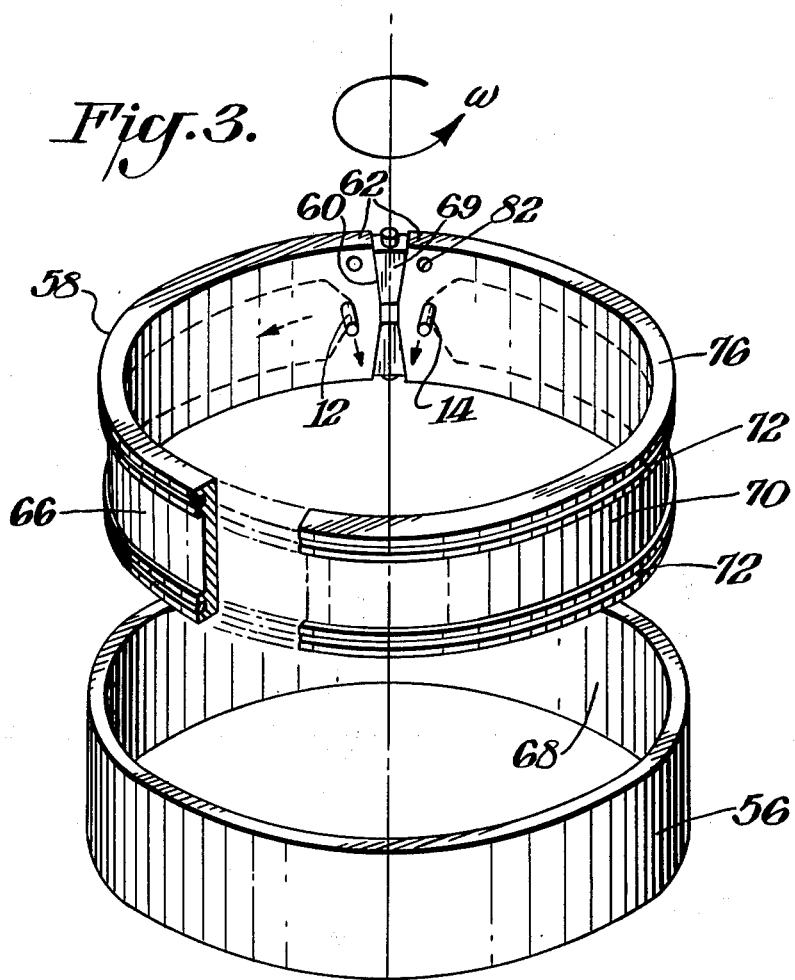
FIG. 3 is an exploded pictorial representation of the mating split rings used to form the channel of this invention.

The principles of operation of a typical sedimentation field flow fractionation apparatus with which this invention finds use may perhaps be more easily understood with reference to FIGS. 1 and 2. In FIG. 1 there may be seen an annular ringlike (even ribbonlike) channel 10 having a relatively small thickness (in the radial dimension) designated W. The channel has an inlet 12 in which the mobile phase or liquid is introduced together with, at some point in time, a small sample of a particulate to be fractionated, and an outlet 14. The annular channel is spun in either direction. For purposes of illustration the channel is illustrated as being rotated in a counterclockwise direction denoted by the arrow 16. Typically these channels may be in the order of magnitude of 0.025 cm; actually, the smaller the channel thickness, the greater rate at which separations can be achieved and the greater the resolution of the separations.

In any event, because of the thin channel, the flow of the liquid is laminar and it assumes a parabolic flow velocity profile across the channel thicknesses, as denoted by the reference numeral 18. The channel 10 is defined by an outer surface or wall 22 and an inner surface or wall 23. If now a radial centrifugal force field F, denoted by the arrow 20, is impressed transversely, that is at right angles to the channel, particulates are compressed into a dynamic cloud with an exponential concentration profile, whose average height or distance from the outer wall 22 is determined by the equilibrium between the average force exerted on each particulate by the field F and by the normal opposing diffusion forces due to Brownian motion. Because the particulates are in constant motion at any given moment, any given particulate can be found at any distance from the wall. Over a long period of time compared to the diffusion time, every particulate in the cloud will have been at every different height from the wall many times. However, the average height from the wall of all of the individual particulates of a given mass over that time period will be the same. Thus, the average height of the particulates from the wall will depend on the mass of the particulates, larger particulates having an average height $1_A$ (FIG. 1) and that is less than that of smaller particulates $1_B$ (FIG. 1).

If one now causes the fluid in the channel to flow at a uniform speed, there is established a parabolic profile of flow velocity 18. In this laminar flow situation, the closer a liquid layer is to the wall, the slower it flows. During the interaction of the compressed cloud of particulates with the flowing fluid, the sufficiently large particulates will interact with layers of fluid whose average speed will be less than the maximum for the entire liquid flow in the channel. These particulates then can be said to be retained or retarded by the field or to show a delayed elution in the field. This mechanism is described by Berg and Purcell in their article entitled "A Method For Separating According to Mass a Mixture of Macromolecules or Small Particles Suspended in a Fluid", I-Theory, by Howard C. Berg and Edward M. Purcell, Proceedings of the National Academy of Sciences, Vol. 58, No. 3, pages 862–869, September 1967.

According to Berg and Purcell, a mixture of macromolecules or small particulates suspended in a fluid may be separated according to mass, or more precisely what may be termed effective mass, that is, the mass of a particulate minus the mass of the fluid it displaces. If the particulates are suspended in the flowing fluid, they distribute themselves in equilibrium "atmospheres" whose scale heights, 1, depend on the effective masses, $m_e$, through the familiar relation $m_e a = kT$. In this relationship k is Boltzmann's constant, T is the absolute temperature, and a is the centrifugal acceleration. In view of this differential transit time of the particulates through a relatively long column or channel, the particulates become separated in time and elute at different times. Thus, as may be seen in FIG. 1, a cluster of relatively small particulates $1_B$ is ahead of and elutes first from the channel, whereas a cluster of larger, heavier particulates $1_A$ is noticed to be distributed more closely to the outer wall 22 and obviously being subjected to the slower moving components of the fluid flow will elute at a later point in time.

In accordance with this invention, in order to reduce the elution times, the channels are made to have an extremely small, constant thickness dimension W. Further, this channel, as noted, must have a relatively smooth finish to prevent the particles from sticking or being trapped in a crevice and to maintain expected retention characteristics under a force field. The channel must be accessable for cleaning and must have a relatively constant thickness to maintain resolution even in the presence of relatively large centrifugal force fields.

These desirable characteristics are accomplished by a system constructed in accordance with this invention depicted in FIG. 2. In this figure, the channel 10 may be disposed in a bowl-like or ringlike rotor 26 for support. The rotor 26 may be part of a conventional centrifuge, denoted by the dashed block 28, which includes a suitable centrifuge drive 30 of a known type operating through a suitable linkage 32, also a known type, which may be direct belt or gear drive. Although a bowl-like rotor is illustrated, it is to be understood that the channel 10 may be supported by rotation about its own cylinder axis by any suitable means such as a spider (not shown) or simple ring. The channel has a liquid or fluid inlet 12 and an outlet 14 which is coupled through a rotating seal 28 of conventional design to the stationary apparatus which comprise the rest of the system. Thus the inlet fluid (or liquid) or mobile phase of the system is derived from suitable solvent reservoirs 30 which are coupled through a conventional pump 32 thence through a two-way, 6-port sampling valve 34 of conventional design through the rotating seal 28 to the inlet 12.

Samples whose particulates are to be separated are introduced into the flowing fluid stream by this conventional sampling valve 34 in which a sample loop 36 has either end connected to opposite ports of the valve 34 with a syringe 38 being coupled to an adjoining port. An exhaust receptacle 40 is coupled to the final port. When the sampling valve 34 is in the position illustrated by the solid lines, sample fluid may be introduced into the sample loop 36 with sample flowing through the sample loop to the exhaust receptacle 40. Fluid from the solvent reservoirs 30 in the meantime flows directly through the sample valve 34. When the sample valve 34 is changed to a second position, depicted by the dashed lines 42, the ports move one position such that the fluid stream from the reservoir 30 now flows through the sample loop 36 before flowing to the rotating seal 28. Conversely the syringe 38 is coupled directly to the exhaust reservoir 40. Thus the sample is carried by the fluid stream to the rotating seal 28.

The outlet line 14 from the channel 10 is coupled out through the rotating seal 28 to a conventional detector 44 and thence to an exhaust or collector receptacle 46. The detector may be any of the conventional types, such as an ultraviolet absorption or a light scattering detector. In any event, the analog electrical output of this detector may be connected as desired to a suitable recorder 48 of known type and in addition may be connected as denoted by the dashed line 50 to a suitable computer for analyzing this data. This system may be automated, if desired, by allowing the computer to control the operation of the pump 32 and also the operation of the centrifuge 28. Such control is depicted by the dashed lines 52 and 54, respectively.

Figure 4:
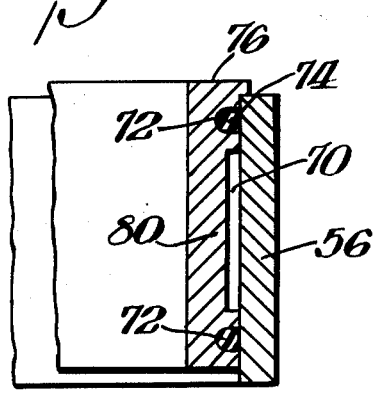
FIG. 4 is a cross sectional view of the mating split rings depicted in FIG. 3.
Figure 5:
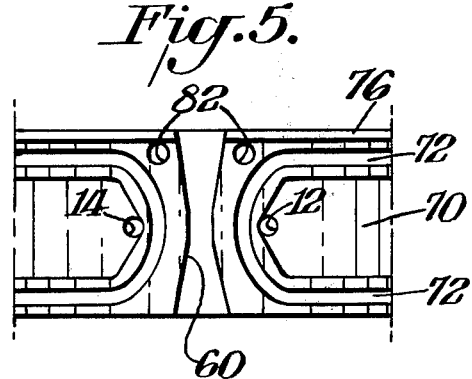
FIG. 5 is a partial pictorial representation of one end of the inner ring, particularly depicting the seal.

The channel 10 is constructed in accordance with this invention to have a configuration as is particularly depicted in FIGS. 3, 4 and 5. It is annular in configuration such that fluid flows circumferentially through the channel. The channel is comprised particularly of an outer ring 56, which is in the form of a band having a constant radius, and functions to provide strength to support an inner ring. Actually, the outer ring may be supported by a spider, bowl, or disc which is driven directly by the centrifuge drive 32 (FIG. 2). Alternatively, the outer ring may be eliminated and the bowl rotor substituted. In this event, the bowl rotor has a flattened inner surface formed thereon to provide the outer channel wall. The outer ring need not be separately mounted inside a support structure (26 of FIG. 2).

The inner ring 58 is split, i.e., its longitudinal circumference is divided or separated to have a gap 60 with the longitudinal ends 62 of the inner ring 58 slightly tapered so as to facilitate the use of a wedge 64. The wedge 64 retains the inner ring sufficiently expanded so as to maintain contact with the outer ring 56 at all times even when stopped. The radially outer wall 66 of the inner ring 58 and the radially inner wall 68 of the outer ring 56 are formed to have a microfinish. This may be accomplished by polishing, for example, or by coating the surfaces with a suitable material either directly or by use of an insert. This smooth finish tends to reduce the possibility that particles will stick to the walls or become entrapped in small crevices or depressions of a depth equal to the average cluster depth 1 of the particle cloud and also insures that the expected sample retention takes place. Depending upon the needs of the operation, a groove 70 may be formed in the outer wall 66 of the inner ring 58 so as to form the flow channel itself or the conduit itself through which the fluid may flow. Along the edges of the main groove 70, subsidiary grooves 72 may be formed to accommodate a resilient seal 74 such as an O-ring which completely surrounds and tracks along the entire edges of the channel, including the end sections as may be seen most clearly in FIG. 5. Actually, at the end sections the groove is generally curved as at 73. Additionally, the upper edge of the inner ring is formed with a radial outwardly extending flange 76, as is seen most clearly in FIG. 4, such that the inner ring may rest upon and be supported by the outer ring against axially downward displacement. This then permits the formation of the narrow flow passage or channel itself which may be designated by the reference numeral 80 as is seen most clearly in FIG. 4. As noted, the thickness W of this channel 80 is relatively small, typically being in the order of 0.1 cm or less, the dimension of the channel, both width and thickness must be very precisely maintained. The actual thickness is selected according to the separations to be performed as is known.

With this arrangement it is seen that the inner ring itself may be formed with the required walls having a high degree of finish. As required further, it may be readily disassembled for cleaning simply by removing the wedge 64 and removing the inner ring from the outer ring. Since the inner ring is made in two parts, its thickness may be closely controlled during manufacture so that there is constant thickness over the entire surface areas of the ring.

To complete the channel construction, either end of the channel 80 is provided with an inlet orifice 12 in the form of a bore through the inner ring and an outlet orifice 14, also in the form of a bore through the inner ring 58. If desired, spanner holes 82 may be formed in the inner ring to facilitate disassembly of the channel. This mating ring arrangement is such that the nature of radial expansion of the inner ring aids in compensating for the normally greater expansion of the outer ring such that the seal is enhanced and fluid loss is reduced. If these rings were affixed solid ring construction, the differential dimensional change would have been such as to at the very least change the separatory characteristics of the channel causing the loss of resolution and retention and in the extreme would have resulted in a fluid loss. The splitting of the ring allows the inner ring to conform more precisely to the extended outer ring shape whatever it may be and to maintain, to a high degree, the channel thickness relatively constant. Further, the channel is more easily cleaned and a better surface in the flow channel is achieved.

I claim:

1. In an apparatus for separating particulates suspended in a fluid medium according to their effective masses, said apparatus having an annular cylindrical channel with a cylinder axis, means for rotating said channel about said axis, means for passing said fluid medium circumferentially through said channel, and means for introducing said particulates into said medium for passage through said channel, the improvement wherein said channel comprises:
    an outer support ring having a constant inner radius, and
    a unitary inner ring, separated at one point along its circumference, mating with said outer ring to define said channel there between.

2. An apparatus of claim 1 wherein said inner ring has an outer wall, the middle portion of which defines a circumferential groove of constant depth.

3. An apparatus of claim 2 wherein a resilient circumferential seal is positioned between said rings along the edges of said channel, thereby to seal said channel.

4. An apparatus of claim 1, 2 or 3, which includes an orifice through said inner ring at each end of said channel thereby to afford fluid access to said channel.

5. An apparatus of claim 4 wherein said inner ring has a circumferential, radial flange defining an L-shaped cross-section, whereby said inner ring flange is axially supported by said outer ring.

6. An apparatus of claim 5 which includes a wedge frictionally engaging each longitudinal end of said inner ring, thereby to maintain said ring spread to contact said outer ring at all times.

7. An apparatus of claim 1 wherein a resilient circumferential seal is positioned between said rings along the edges of said channel, thereby to seal said channel.

8. An apparatus of claim 7 which includes an orifice through said inner ring at each end of said channel thereby to afford fluid access to said channel.

9. An apparatus of claim 1 wherein said inner ring has a circumferential, radial flange defining an L-shaped cross-section, whereby said inner ring flange is axially supported by said outer ring.

10. An apparatus of claim 9 which includes a wedge frictionally engaging each longitudinal end of said inner ring, thereby to maintain said ring spread to contact said outer ring at all times.

11. An apparatus of claim 9 which includes a wedge frictionally engaging each longitudinal end of said inner ring, thereby to maintain said ring spread to contact said outer ring at all times wherein said apparatus includes a bowl-like rotor adapted to support said channel.

* * * * *